United States Patent [19]

Bajusz et al.

[11] 4,316,889
[45] Feb. 23, 1982

[54] NOVEL PEPTIDYL-ARGININE ALDEHYDE DERIVATIVES AND PROCESS FOR THE PREPARATION THEREOF

[75] Inventors: Sándor Bajusz; Erzsébet Széll née Hasenöhrl; Éva Barabas; Dániel Bagdy, all of Budapest, Hungary

[73] Assignee: Richter Gedeon Vegyészeti Gyár Rt., Budapest, Hungary

[21] Appl. No.: 108,224

[22] Filed: Dec. 28, 1979

[30] Foreign Application Priority Data

Jan. 4, 1979 [HU] Hungary .............................. GO-1435

[51] Int. Cl.³ ..................... A61K 37/00; C07C 103/52
[52] U.S. Cl. ............................ 424/177; 260/112.5 R
[58] Field of Search ................... 260/112.5 R; 424/177

[56] References Cited

FOREIGN PATENT DOCUMENTS 169870 6/1974 Hungary ...................... 260/112.5 R
4941418 10/1970 Japan .................................. 424/177

OTHER PUBLICATIONS

Chem. Abstr. vol. 83, 1975, p. 10882s.

*Primary Examiner*—Delbert R. Phillips
*Attorney, Agent, or Firm*—Karl F. Ross

[57] ABSTRACT

Novel peptidyl-arginine aldehyde derivatives and their salts of formula I,

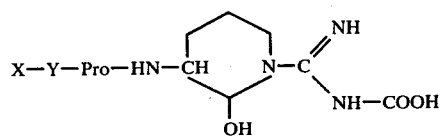

wherein X represents a hydrogen atom, benzoyl or tert-butyloxycarbonyl group, and Y is a D-phenylalanine, β-phenyl-D-lactic acid or D-allo-isoleucine moiety, are prepared from peptidyl-arginine aldehydes protected by an urethane type protecting group on their N- or O-terminal and/or a guanidino group, by removing the protecting group in a mixture of lower alkanols and water by means of hydrogenolysis, and eventually converting the product formed into a salt.

The compounds of formula I possess valuable antithrombin activity.

4 Claims, No Drawings

NOVEL PEPTIDYL-ARGININE ALDEHYDE DERIVATIVES AND PROCESS FOR THE PREPARATION THEREOF

FIELD OF THE INVENTION

The invention relates to novel peptidyl-arginine aldehyde derivatives and their salts of formula I or Ia

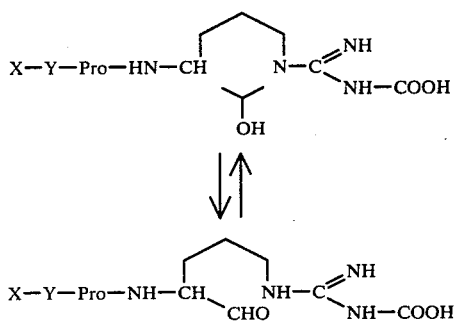

wherein,

X is hydrogen, benzoyl or tert-butyloxycarbonyl, and Y is a D-phenylalanine, β-phenyl-D-lactic acid or D-allo-isoleucine moiety.

Furthermore the invention relates to a process for preparing these compounds.

BACKGROUND OF THE INVENTION

It is known that peptide aldehydes of specific structure have the ability to inhibit the proteolytic reactions of serine or cysteine enzymes. The mechanism of enzyme inhibition is assumed to be an addition reaction between the reactive OH or SH group of the enzyme and the -CH=O group of peptide aldehydes, the hemiacetal formed upon addition being the "non-productive" analogue of the tetrahedral transitory complex formed in the course of enzyme-substrate interaction (Westernik and Wolfenden: J. Biol. Chem. 247, 8195 (1972)). The first members of this family of compounds were the leupeptines of natural origin, i.e. acetyl- and propionyl-L-leucyl-L-leucyl-arginine aldehyde hydrochlorides, which were both capable to inhibit plasmin, trypsin and papain (Kawamura et al.: Chem. Pharm. Bull. 17, 1902 (1969); H. Umezawa: Enzyme Inhibitors of Microbial Origin, University Park Press, Baltimore-London-Tokyo, 1972, pp. 17 to 29). Other peptidyl-arginine aldehydes, e.g. benzoyl-D-allo-isoleucyl-L-prolyl-L-arginine aldehyde p-toluenesulfonate and D-phenylalanyl-L-prolyl-L-arginine aldehyde acetate, exhibit marked antithrombin activity (Hungarian Patent No. 169,870).

On the basis of the NMR studies of leupeptines it was assumed that the acyl-arginine aldehyde hydrochlorides are mixtures of varying composition (Maeda et al.: J. Antibiotics (Tokyo), 24, 402/1971/; Kawamura et al.: Chem. Pharm. Bull., 17, 1902 (1969). In addition to the acyl-arginine aldehyde hydrochloride there are two other components present, the aldehyde hydrate as well as the cyclic carbinolamine. As regards these components the aldehyde hydrate cannot directly participate in hemiacetal formation leading to enzyme inhibition (Westernik and Wolfenden: J. Biol. Chem. 247, 8195/1972/). This ever varying rate and grade of aldehyde hydrate formation may be the cause of the recently observed phenomenon that both the enzyme inhibitory activity of the above synthetic compounds and the antithrombin effect of D-phenylalanyl-L-prolyl-L-arginine aldehyde acetate or hydrochloride for instance, are changing, and that their potency is reduced upon standing in solution [tris-(hydroxy-methyl)-methylamine hydrochloride, i.e. TRIS/HCl buffer, pH=7.4].

OBJECT OF THE INVENTION

It is the object of the present invention to provide a novel process for preparing peptidyl-arginine aldehyde derivatives having, compared to hitherto described results, higher enzyme inhibitory activity and improved stability.

DESCRIPTION OF THE INVENTION

It has been found that upon the deblocking of peptidylarginine aldehydes, protected by an urethane type protecting group, e.g. a benzyloxycarbonyl group, carried out in neutral medium, compounds of formula I, wherein X and Y have the same meaning as above, are formed. For example upon the hydrogenolysis of benzyloxycarbonyl-D-phenylalanyl-L-prolyl-$N^G$-benzyloxycarbonyl-L-arginine aldehyde ($N^G$ means the ω nitrogen atom of the arginine side-chain), carried out in the absence of acid or base, D-phenylalanyl-L-prolyl-$N^G$-carboxy-L-arginine aldehyde is formed (in formula I X is H and Y is a D-phenylalanine moiety, while as it is widely known, the hydrogenolysis of peptidyl-arginine aldehydes, protected by a benzyloxycarbonyl group, performed in a basic medium, and subsequent salt formation yields free peptidylarginine aldehyde salts. Thus H-D-Phe-Pro-Arg-H acetate or hydrochloride were obtained from Z-D-Phe-Pro-Arg[Z]-H in this was (Hungarian Patent No. 169,870).

The above abbreviations used for amino acid residues or moieties and peptide derivatives conform to those established in the literature (i.e. J. Biol. Chem. 247, 977 (1972), Z, BOC and Bz representing benzyloxycarbonyl, tertiary butyloxycarbonyl, and benzoyl groups, respectively, while Arg(Z) and Arg(COOH) represent $N^G$-benzyloxycarbonyl and $N^G$-carboxy-L-arginine residues, respectively.

It also has been found that the enzyme inhibitory effect of tripeptide aldehyde derivatives of formula I is unexpectedly higher and more stable than that of the free tripeptide aldehyde salt of corresponding amino acid sequence. Thus H-D-Phe-Pro-Arg(COOH)-H possesses a higher antithrombin activity, and exerts an increased inhibitory effect on the thrombin-fibrinogen reaction compared to H-D-Phe-Pro-Arg-H hydrochloride or acetate, the inhibitory activity of the latter varying according to synthesis conditions. Stored in a buffer solution (pH=7.4) for 20 hours the antithrombin activity of $N^G$-carboxy-tripeptide aldehyde of formula I is practically unchanged while that of the corresponding free tripeptide aldehyde salts is reduced to 10 to 20 percent of the initial potency.

It is a further unexpected property of $N^G$-carboxy-tripeptide aldehydes of formula I that their inhibitory potency can be increased by partial protonation (salt formation). Thus the hemihydrochloride of D-phenylalanyl-L-prolyl-$N^G$-carboxy-L-arginine aldehyde exhibits five times the activity of the compound devoid of hydrochloric acid. Though the stability is reduced by the protonation of $N^G$-carboxy-tripeptide aldehydes of formula I, standing in a buffer solution for 20 hours their potency is still higher than that of the free tripeptide aldehyde salts of corresponding amino acid sequence.

Table 1 demonstrates the antithrombin activity, the change in activity following standing in TRIS/HCl buffer (pH=7.4) as well as the relative activity compared to H-D-Phe-Pro-Arg(COOH)-H (the activity of the latter compound being arbitrarily taken as 100) of both D-phenylalanyl-L-prolyl-$N^G$-carboxy-L-arginine aldehyde and its hemihydrochloride of formula I, wherein X represents a H atom and Y a D-phenylalanine residue, and that of two salts of the free tripeptide aldehyde of corresponding amino acid sequence. Antithrombin activity is defined by the amount of drug required for a tenfold increase of the thrombin-time of fibrinogen (thrombintime: time of clotting induced by thrombin).

TABLE 1

Antithrombin Activity of Tripeptide Aldehyde Derivatives

| Peptide derivative | Amount of drug required for tenfold increase of thrombin-time following dissolution of peptide | | | |
|---|---|---|---|---|
| | 0 hour | | 20 hours | |
| | μg/ml | (ra+) | μg/ml | (ra+) |
| H—D-Phe—Pro—Arg(COOH)—H | 0.275 | (100) | 0.300 | (92) |
| H—D-Phe—Pro—Arg(COOH)—H . 0.5 HCl | 0.050 | (550) | 0.350 | (79) |
| H—D-Phe—Pro—Arg—H . 2HCl[a] | 0.35–0.95 | (79–29) | 6.0 | (5) |
| H—D-Phe—Pro—Arg—H . 2 CH₃COOH | 0.37–1.25 | (73–22) | 6.2 | (4) | ra+ = relative activity
[a] product obtained from Z—D-Phe—Pro—Arg(Z)—H by hydrogenolysis carried out in acidic medium Antithrombin activities were assayed in the following system:

0.5 percent bovine fibrinogen (0.2 ml). in 0.9 percent sodium chloride solution, peptide in TRIS/HCl buffer (0.1 ml., pH=7.4), and US Standard Human Thrombin (0.1 ml.) (NIH, Bethesda, Maryland, USA; 5 U/ml.). The clotting time of the system devoid of peptide is 15 seconds.

The results of in vivo studies are demonstrated in the case of D-phenylalanyl-L-prolyl-$N^G$-carboxy-L-arginine aldehyde (X representing a H atom and Y a D-phenylalanine residue in formula I) as a representative example. Trials performed on five species (mouse, rat, rabbit, dog, monkey) have proved that the increased antithrombin activity of the compound of formula I, wherein X represents a H atom and Y a D-phenylalanine residue, is manifested under in vivo conditions, too. This effect is substantial not only at intravenous, intramuscular and subcutaneous but also at oral administration. The in vivo antithrombin activity of H-D-Phe-Pro-Arg(COOH)-H was measured following oral administration of doses of 50 mg./kg. to dogs in a Thromboelastograph (Hellige, Vienna, Austria) where the drug increased the thrombin-time four to sixfold for a period of two hours. The corresponding free tripeptide aldehyde salts, i.e. D-phenylalanyl-L-prolyl-L-arginine aldehyde hydrochloride or acetate, had practically no influence on thrombin-time at identical, 50 mg./kg. oral doses.

Based on the above, the invention provides to a process for preparing novel peptidyl-arginine aldehyde derivatives and their salts of formula I or Ia, wherein X is H, benzoyl or tertiary butyloxycarbonyl, and Y is a D-phenylalanine, β-phenyl-D-lactic acid or D-alloisolaucine residue, from peptidyl-arginine aldehydes protected by an urethane type, preferably benzyloxycarbonyl, protecting group on their N- or O-terminal and/or a guanidino group, comprising the steps of removing the protecting group in a mixture of lower alkanols and water by means of hydrogenolysis and eventually converting the product formed into a salt.

According to the present invention L-arginine lactam, protected by a benzyloxycarbonyl group at its guanidino moiety, is preferably condensed with the corresponding N-acyl-dipeptide, the protected tripeptide lactam thus formed is reduced, and the benzyloxycarbonyl group protecting the guanidino group or eventually both the N-terminal and guanidino group of the resulting tripeptide aldehyde, is cleaved by hydrogenolysis carried out in a mixture of ethanol and water, whereafter ethanol is removed from the solution under reduced pressure, and the aqueous solution is freeze-dried. The residue is eventually dissolved in water and repeatedly freeze-dried following addition of less than one equivalent of acid.

SPECIFIC EXAMPLES

The following Examples illustrate the invention. The $R_F$ values were determined by silica gel thin-layer chromatography (Kieselgel G, Reanal, Budapest) in the following systems:
1. ethyl acetate-pyridine-acetic acid-water-480:20:6:11
2. ethyl acetate-pyridine-acetic acid-water-240:20:6:11
3. ethyl acetate-pyridine-acetic acid-water-60:20:6:11
4. ethyl acetate-pyridine-acetic acid-water-30:20:6:11.

EXAMPLE 1

D-Phenylalanyl-L-prolyl-$N^G$-carboxyl-L-arginine aldehyde (in formula I, X represents a H atom and Y a D-phenylalanine residue)

Step 1: Tert-butyloxycarbonyl-$N^G$-benzyloxycarbonyl-L-arginine lactam 41.1 g. (125 mmoles) of tert-butyloxycarbonyl-L-arginine hydrochloride hydrate (Yamashiro et al.: J. Am. Chem. Soc., 94, 2855 (1972) are dissolved in 125 ml. of 4 N sodium hydroxide and cooled to −5° C. to 0° C. Under vigorous stirring benzyloxycarbonyl chloride (75 ml., 500 mmoles) and 125 ml. of 4 N sodium hydroxide are added to the solution at such a rate that the pH of the mixture never exceeds the value of 10. Stirring is continued at 0° C. for 1.5 hours. The reaction mixture is diluted by 100 ml. of water, extracted three times with 100 ml. of diethyl ether, then is cooled in an ice bath to 4° to 6° C., and acidified with 3 N sulfuric acid to pH=3 (about 130 ml. are needed). The separated product is extracted three times with 250 ml. of ethyl acetate. The combined ethyl acetate extracts are washed twice with 125 ml. of 15 percent sodium chloride solution, dried over sodium sulfate and evaporated under reduced pressure. The residue is worked up with diethyl ether, filtered, washed with diethyl ether and air-dried. Yield: 37.5 g. (76 percent of the theoretical yield) of tertbutyloxycarbonyl-N$^G$-benzyloxycarbonyl-L-arginine; R$_F$=0.17 to 0.27.

This product is dissolved in 130 ml. of tetrahydrofuran. 13.58 ml. (97 mmoles) of triethylamine are added and the mixture is cooled to −10° C. At this temperature and at stirring 12.8 ml. (97 mmoles) of chloroformic acid isobutyl ester are added, and after stirring for 5 minutes 13.6 ml. (97.8 mmoles) of triethyl amine are added. The reaction mixture is stirred for an additional hour at 0° C., then for one hour without cooling, finally is poured into 600 ml. of ice water, the precipitated material is filtered, washed with water and dried over P$_2$O$_5$ under reduced pressure. Yield: 32.7 g. (91 percent of the theoretical amount, 70 percent calculated for BOC-Arg(HCl)-OH.H$_2$O) of the named compound; R$_F$ 0.85 to 0.95, m.p. 162° to 164° C.

Step 2: Benzyloxycarbonyl-D-phenylalanyl-L-prolyl-N$^G$-benzyloxycarbonyl-L-arginine lactam 8.6 g. (22 mmoles) of tert-butyloxycarbonyl-N$^G$-benzyloxycarbonyl-L-arginine lactam (Example 1, Step 1) are suspended in 20 ml. of ethyl acetate and 40 ml. of 4 M HCl-ethylacetate solution are added at 5° C. while stirring. The reaction mixture is stirred for 30 minutes under ice cooling, then is diluted with 100 ml. of cool ethyl acetate, the precipitate formed is filtered, washed with ethyl acetate and dried over potassium hydroxide under reduced pressure. The N$^G$-benzyloxycarbonyl-L-arginine lactam hydrochloride obtained is dissolved in 20 ml. of dimethyl formamide, cooled to −10° C., then combined with 6.2 ml. (44 mmoles) of triethyl amine. The resulting suspension is poured into the following mixed anhydride.

8 g. (20 mmoles) of benzyloxycarbonyl-D-phenylalanine-L-proline (Nikolaides et al.: J. Med. Chem., 11, 74 (1968) are dissolved in 25 ml. of dimethyl formamide, cooled to −15° C. and at this temperature, under vigorous stirring, 2.22 ml. (20 mmoles) of N-methyl-morpholine and 2.64 ml. (20 mmoles) of chloroformic acid isobutyl ester are added. After stirring the mixture for 10 minutes, the above suspension in dimethyl formamide is added, too. The pH of the reaction mixture is adjusted, if necessary to pH=8 to 9 with triethylamine, and stirring is continued for one hour at −15° C. and a further hour at 0° C. Then the mixture is diluted with 50 ml. of benzene, the precipitated salts are filtered and washed twice with 20 ml. of benzene each. The filtrate is diluted with 50 ml. of water, the phases are separated, and the aqueous phase is extracted three times with 20 ml. of benzene each. The combined benzene extracts are washed successively three times with 10 percent sodium carbonate (30 ml.), water (30 ml.), twice with 0.1 N HCl (30 ml.), and finally twice with water (30 ml.). After drying over sodium sulfate the benzene solution is evaporated under reduced pressure, the residue is mixed with 30 ml. of diethyl ether, the diethyl ether is decanted, and the residue is triturated with 30 ml. of petroleum ether, filtered, washed with petroleum ether, finally air-dried. Yield: 11.7 g. (87 percent of the theoretical yield) of the title compound; R$_F^1$=0.72 to 0.78.

Step 3: Benzyloxycarbonyl-D-phenylalanyl-L-prolyl-N$^G$-benzyloxycarbonyl-L-arginine aldehyde 10.05 g. (15 mmoles) of protected tripeptide lactam (Example 1, Step 2) are dissolved in 45 ml. of tetrahydrofuran, and at −20° C., under vigorous stirring, 11.25 mmoles of lithium-aluminum hydride are added in tetrahydrofuran (about 28 ml. from an approximately 0.4 M solution). The progress of reduction is controlled by thin-layer chromatography (R$_F^1$=0.72 to 0.78 for the lactam, and 0.32 to 0.40 for the aldehyde), and if required a further portion of the hydride solution is added. At the end of the reaction the tetrahydrofuran solution is cautiously acidified with 1 N hydrochloric acid to pH=2, diluted with water in such a way that no precipitate is formed (about 100 ml.) and extracted twice with n-hexane (30 ml.). The aqueous tetrahydrofuran solution is extracted three times with methylene chloride (75 ml.), the combined methylene chloride extracts are washed first with a 10 percent sodium carbonate solution (3×10 ml.) then with water (2×10 ml.). The methylene chloride solution is dried over sodium sulfate and evaporated under reduced pressure. The residue is dissolved in 50 ml. of benzene and evaporated under reduced pressure. This dissolving in benzene and evaporation is repeated. The residue is triturated with diethyl ether, filtered, washed with diethyl ether, and air-dried. Yield: 7.3 g. (72 percent of the theoretical yield) of the named compound; R$_F^1$=0.32 to 0.40; m.p. 116° to 117° C.

Step 4: D-Phenylalanyl-L-prolyl-N$^G$-carboxy-L-arginine aldehyde 6.7 g. (10 mmoles) of protected tripeptide aldehyde (Example 1, Step 3) are dissolved in 75 percent aqueous ethanol (100 ml.) and subjected to hydrogenolysis in the presence of 10 percent palladium-charcoal (1 g.). The reaction is controlled by thin-layer chromatography (the R$_F^4$ values of the protected tripeptide aldehyde and the free N$^G$-carboxy derivative are 0.90 to 0.95, and 0.35 to 0.40, resp.). At the end of the reaction the catalyst is filtered off, washed with water (30 ml.), and the filtrate is evaporated to about 30 to 40 ml, under reduced pressure (evaporation of ethanol). The residue is diluted with 100 ml. of water, the aqueous solution is extracted with 30 ml. of methylene chloride and subsequently freeze-dried. Yield: 4.3 g. of the named compound; R$_F^4$=0.35 to 0.40; $[\alpha]_D^{20}$=−.123±1° (c=1, water); amino acid analysis: Phe=1.02; Arg-H=0.97 (assayed as NH$_3$); Pro=1.00 (base). Molecular weight calculated on the basis of the amino acid analysis=471. CO$_2$=10.9 percent (liberated with sulfuric acid) and 2.1 percent (precipitated as BaCO$_3$).

EXAMPLE 2

D-Phenylalanyl-L-prolyl-N$^G$-carboxy-L-arginine aldehyde hemihydrochloride 0.48 g. of N$^G$-carboxy-D-phenylalanyl-L-prolyl-L-arginine aldehyde are dissolved in 5 ml. of water and at 3° to 5° C. 0.1 N hydrochloric acid (5 ml.) is added. The solution is freeze-dried. Yield: 0.45 g. of the named compound. R$_F^4$=0.35 to 0.40, $[\alpha]_D^{20}$=−120° (c=1, water).

EXAMPLE 3

Tert-butyloxycarbonyl-D-phenylalanyl-L-prolyl-N$^G$-carboxy-L-arginine aldehyde (in Formula I, X is the tertiary butyloxycarbonyl moiety and Y is the D-phenylalanine moiety)

Step 1: Tert-butyloxycarbonyl-D-phenylalanyl-L-prolyl-N$^G$-benzyloxycarbonyl-L-arginine lactam Starting from 8.6 g. (22 mmoles) of tert-butyloxycarbonyl-N$^G$-benzyloxycarbonyl-L-arginine lactam, N$^G$-benzyloxycarbonyl-L-arginine lactam is prepared according to the procedure described in Example 1, Step 2, and the dimethylformamide suspension obtained is added to the following mixed anhydride.

7.25 g. (20 mmoles) of tert-butyloxycarbonyl-D-phenylalanyl-L-proline (U. Ludescher and R.

Schwyzer: Helv. Chim. Acta 55, 2052 (1972) and 2.22 ml. (20 mmoles) of N-methyl-morpholine are dissolved in 20 ml. of dimethyl formamide. The solution is cooled to −15° C., stirred, then 2.64 ml. (20 mmoles) of isobutyl chloroformate and after 5 minutes the above dimethyl formamide solution are added. The reaction mixture is stirred for one hour at −15° C. and for an additional one hour at 0° C., then it is diluted with 30 ml. of benzene. The precipitated salts are filtered and washed twice with benzene (10 ml.). The benzene-dimethylformamide solution is diluted with 50 ml. of water and the phases are separated. The aqueous phase is extracted twice with benzene (10 ml.), then the combined benzene extracts are washed successively with 10 percent sodium carbonate (3×30 ml.), water (30 ml.), 0.5 N sulfuric acid (3×30 ml.) and water (2×30 ml.), dried over sodium sulfate and evaporated under reduced pressure. The residue is worked up with light petroleum, filtered, washed with light petroleum and air-dried. Yield: 9.65 g. (76 percent of the theoretical yield) of the named compound; $R_F^1 = 0.81$ to 0.89.

Step 2: Tert-butyloxycarbonyl-D-phenylalanyl-L-prolyl-$N^G$-benzyloxycarbonyl-L-arginine aldehyde Starting from 9.52 g. (15 mmoles) of protected tripeptide lactam (Example 3, Step 1) the process described in Example 1, Step 3 was carried out, except that after the lithium-aluminium-hydride reduction acidification was performed with 0.5 N sulfuric acid. Yield: 6.9 g. (72 percent of the theoretical yield) of the named compound; $R_F^2 = 0.46$ to 0.56.

Step 3: Tert-butyloxycarbonyl-D-phenylalanyl-L-prolyl-$N^G$-carboxy-L-arginine aldehyde Starting from 6.4 g. (10 mmoles) of protected tripeptide aldehyde (Example 3, Step 2) the procedure described in Step 4 of Example 1 is used. Yield: 5.1 g. (85 percent of the theoretical yield) of the named compound; $R_F^3 = 0.46$ to 0.56; $[\alpha]_D^{20} = -64 \pm 1°$ (c=1, aqueous solution, pH adjusted with hydrochloric acid to 7). Amino acid analysis: Phe=0.96; Arg-H=0.97 (measured in the form of NH$_3$); Pro=1.00 (basis). Molecular weight calculated on the basis of amino acid analysis: 570. $CO_2$=10.1 percent (liberated with sulfuric acid), and 3.1 percent (precipitated as $BaCO_3$),

EXAMPLE 4

Benzoyl-D-allo-isoleucyl-L-prolyl-$N^G$-carboxy-L-arginine aldehyde (in Formula 1, X is a benzoyl group and Y is a D-allo-isoleucine residue)

Step 1: Benzoyl-D-allo-Isoleucyl-L-proline dicyclohexyl-ammonium salt 19.2 g. (81.5 mmoles) of benzoyl-L-isoleucine (F. Ehrlich: Berichte 37, 1809 (1904) and 16.5 g. (80 mmoles) of dicyclohexyl-carbodiimide are dissolved in 150 ml. of methylene chloride cooled to 5° to 10° C. The solution is stirred in an ice bath for two hours, then 2 ml. of triethyl amine and 100 ml. of petroleum ether are added. The precipitated dicyclohexyl-urea is filtered off and washed with petroleum ether (2×20 ml.). The filtrate is extracted with water (2×50 ml.), 5 percent sodium hydrogen carbonate solution (2×50 ml.) and water, dried over sodium sulfate and evaporated at reduced pressure. The residue is dissolved in 80 ml. of pyridine, then 9.2 g. (80 mmoles) of L-proline and 22.4 ml. (160 mmoles) of triethylamine are added to the solution. The reaction mixture is stirred at room temperature for six hours, then is evaporated under reduced pressure. The residue is dissolved in a mixture of water (100 ml.) and ether (50 ml.), the aqueous phase is washed twice with ether (20 ml.), and the combined ether extracts are washed twice with water (20 ml.). The aqueous phases are combined and acidified with 5 N sulfuric acid to pH=2. The separated oil is extracted three times with ethyl acetate (50 ml.), the combined ethyl acetate is washed twice with water (20 ml.), dried over sodium sulfate and evaporated under reduced pressure. The residue is dissolved in 100 ml. of ether, thereafter 16 ml. of dicyclohexyl amine are poured to the solution. The crystals formed are filtered, washed with ether (3×20 ml.) and dried over concentrated sulfuric acid in vacuo. Yield 26.3 g. (64 percent of the theoretical yield) of the named compound. M.p. 117° to 118° C. $R_F^1 = 0.36$ to 0.46 and 0.13 to 0.23 (dicyclohexylamine). Amino acid analysis: proline: 1.00 (base); allo-isoleucine: 0.92; isoleucine: 0.02.

Step 2: Benzoyl-D-allo-isoleucyl-L-prolyl-$N^G$-benzyloxycarbonyl-L-arginine lactam Starting from 8.6 g. (22 mmoles) of tert-butyloxycarbonyl-$N^G$-benzyloxycarbonyl-L-arginine lactam, $N^G$-benzyloxycarbonyl-L-arginine lactam is prepared according to the procedure described in Step 2 of Example 1, and the dimethyl formamide suspension obtained is added to the following mixed anhydride.

10.3 g. (20 mmoles) of benzoyl-D-allo-isoleucyl-L-proline dicyclohexyl-ammonium salt (Example 4, Step 1), and 0.23 ml. (2 mmoles) of N-methyl-morpholine are dissolved in 20 ml. of dimethyl formamide, cooled to −15° C. and at constant stirring first 2.64 ml. (20 mmoles) of isobutyl chloroformate, then after 5 minutes the above dimethyl formamide solution are added. The reaction mixture is stirred for one hour at −15° C. and for an additional hour at 0° C. The precipitated salts are filtered and washed with dimethyl formamide (2×5 ml.). The combined filtrates are diluted with 100 ml. of benzene and the benzene phase is washed with water (3×30 ml.), 1 N sodium hydroxide (2×20 ml.), water (3×30 ml.), 0.5 N sulfuric acid (2×20 ml.) and water (3×20 ml.), dried over sodium sulfate and evaporated under reduced pressure. The residue is triturated with petroleum ether, filtered, washed with petroleum ether and air-dried. Yield 9.3 g. (76 percent of the theoretical yield) of the named product; $R_F^1 = 0.52$ to 0.62.

Step 3: Benzoyl-D-allo-isoleucyl-L-prolyl-$N^G$-benzyloxycarbonyl-L-arginine aldehyde 9.2 g. (15 mmoles) of protected tripeptide lactam (Example 4, Step 2) are dissolved in 40 ml. of tetrahydrofuran and at −20° C. and constant stirring 0.427 g. (11.25 mmoles) of lithium-aluminum-hydride, dissolved in tetrahydrofuran, are added. The reaction mixture is acidified to pH=2 with 1 N hydrochloric acid, then is diluted with 80 ml. of water. The solution is washed with 30 ml. of n-hexane, and extracted with methylene chloride (3×50 ml.). The combined methylene chloride extracts are washed with a 10 percent aqueous sodium carbonate solution (2×10 ml.) and water (2×10 ml.), and are evaporated under reduced pressure after drying over sodium sulfate. The residue obtained is worked up with diethyl ether, and dried over concentrated sulfuric acid in vacuo. Yield: 6.7 g. (72 percent of the theoretical yield) of the named product; $R_F^1 = 0.47$ to 0.57.

Step 4: Benzoyl-D-allo-isoleucyl-L-prolyl-$N^G$-carboxy-L-arginine aldehyde 6.2 g. (10 mmoles) of protected tripeptide aldehyde are subjected to hydrogenolysis according to the procedure described in Step 4 of Example 1, and subsequently isolated and freeze-dried. Yield: 4.05 g. (81 percent of the theoretical yield) of the named product; $R_F^3 = 0.4$ to 0.5; $[\alpha]_D^{20} = -42.6 \pm 1°$ (c=1, in an aqueous solution where the pH is adjusted to 7 with hydrochloric acid). Amino acid analysis: allo-Ile: 0.97; Ile: 0.02; Arg-H: 0.95 (measured in the form of NH$_3$); Pro: 1.00 (base). Molecular weight calculated on the basis of amino acid analysis: 590. CO$_2$=9.5 percent (liberated with sulfuric acid) and 2.0 percent (precipitated in the form of BaCO$_3$).

EXAMPLE 5

β-Phenyl-D-lactyl-L-prolyl-N$^G$-carboxy-L-arginine (in Formula I, X is hydrogen and Y is a β-phenyl-D-lactic acid residue)

Step 1: O-tert-butyloxycarbonylamido-β-phenyl-D-lactyl-L-proline 15.1 g. (40 mmoles) of O-tertiary-butyl-oxycarbonylamido-β-phenyl-D-lactic acid N-hydroxysuccinimid ester (Kisfaludy et al.: Acta Biochim. Biophys. Acad. Sci. Hung., 6, 393 (1972) are dissolved in pyridine (50 ml.) and mixed with 4.7 g. (40 mmoles) of L-proline and 5.6 ml. (40 mmoles) of triethyl amine, until dissolution becomes complete. Then the reaction mixture is evaporated under reduced pressure. The residue is taken up in a mixture of water (100 ml.) and diethyl ether (100 ml.). The aqueous phase is washed with diethyl ether (30 ml.), and the combined ether extracts with water (30 ml.). The aqueous phases are combined, acidified with 3 N hydrochloric acid to pH=2, and extracted with ethyl acetate (3×50 ml.). The combined ethyl acetate extracts are washed with water (2×20 ml.), dried over sodium sulfate, and evaporated to dryness under reduced pressure. Yield: 9.85 g. (65 percent of the theoretical yield) of the named compound; $R_F^2$=0.4 to 0.5.

Step 2: O-tert-Butyloxycarbonylamido-β-phenyl-D-lactyl-L-prolyl-N$^G$-benzyloxycarbonyl-L-arginine lactam 11.2 g. (28.6 mmoles) of tert-butyloxycarbonyl-N$^G$-benzyloxycarbonyl-L-arginine lactam (Example 1, Step 1) are suspended in 25 ml. of ethyl acetate and while stirring at 5° C. 4 M hydrochloric acid-ethylacetate (50 ml.) is poured into the mixture. Stirring is continued for an additional 30 minutes in an ice bath, then the reaction mixture is diluted with 130 ml. of refrigerated ethyl acetate and dried over potassium hydroxide in vacuo. The N$^G$-benzyloxycarbonyl-L-arginine lactam hydrochloride obtained is dissolved in 25 ml. of dimethyl formamide, cooled to −10° C. and 8.1 ml. (57.8 mmoles) of triethyl amine are added. The suspension obtained is poured into the following mixed anhydride.

9.85 g. (26 mmoles) of O-tertiary-butyl-oxycarbonylamido-β-phenyl-D-lactyl-L-proline, prepared according to the procedure described in Step 1 of Example 5, are dissolved in 33 ml. of dimethyl formamide, cooled to −15° C. and at this temperature and while vigorous stirring first 2.89 ml. (26 mmoles) of N-methyl-morpholine and 3.43 ml. (26 mmoles) of isobutyl chloroformate, then after stirring for an additional 10 minutes the above dimethyl formamide suspension are added. The pH is adjusted, if required, to 8 to 9 with triethyl amine, and stirring is continued for one hour at −15° C. and for a further hour at 0° C. The reaction mixture is diluted with 60 ml. of benzene, the precipitated salts are filtered and washed with benzene (2×30 ml.). 70 ml. of water are added to the filtrate, the phases are separated, and the aqueous phase is washed with 3×30 ml. of benzene. The combined benzene extracts are washed with 10 percent sodium carbonate (3×40 ml.), water (3×40 ml.), 0.1 N hydrochloric acid (2×40 ml.) and finally water (2×40 ml.), dried over sodium sulfate and evaporated under reduced pressure. The residue is worked up with light petroleum, filtered, washed with light petroleum, and air-dried. Yield: 10.3 g. (60 percent of the theoretical yield) of the named product; $R_F^2$=0.65 to 0.70

Step 3: O-tert-Butyloxycarbonylamido-β-phenyl-D-lactyl-L-prolyl-N$^G$-benzyloxycarbonyl-L-arginine aldehyde Starting from 10.2 g. (15 mmoles) of protected tripeptide lactam (Example 5, Step 2) the procedure described in Step 3 of Example 1 is followed, except that at the end the evaporation residue is worked up with 1:1 mixture of diethylether and light petroleum, filtered and washed with the same solvent. Yield: 6.4 g. (62 percent of the theoretical yield) of the named compound; $R_F^2$=0.32 to 0.42.

Step 4: D-Phenyl-D-lactyl-L-prolyl-N-carboxy-L-arginine aldehyde 6.2 g. (9 mmoles) of protected tripeptide aldehyde (Example 5, Step 3) are dissolved in 75 percent aqueous ethanol (100 ml.), and subjected to hydrogenolysis in the presence of 10 percent palladium-charcoal (1 g.). The progress of the reaction is controlled by thin-layer chromatography (the $R_F^4$ values of the protected tripeptide aldehyde and the N$^G$-carboxy derivative were 0.92 to 0.97, and 0.56 to 0.66, respectively). By the end of the reaction the catalyst is filtered, washed with water (30 ml.), and the filtrate is concentrated at reduced pressure to 30 to 40 ml. The residue is diluted with 100 ml. of water, the aqueous solution is extracted with 30 ml. of methylene chloride and freeze-dried. Yield: 3.8 g. of the named product; $R_F^4$=0.56 to 0.66. $[\alpha]_D^{20} = -81 \pm 1°$ (c=1, water). Amino acid analysis: Arg-H: 0.96 (measured in the form of NH$_3$); Pro: 1.00 (base). Molecular weight calculated on the basis of amino acid analysis: 470. CO$_2$=9.6 percent (liberated with sulfuric acid) and 1.3 percent (precipitated in the form of BaCO$_3$).

What we claim is:

1. A peptidyl-arginine aldehyde derivative of the formula I or Ia

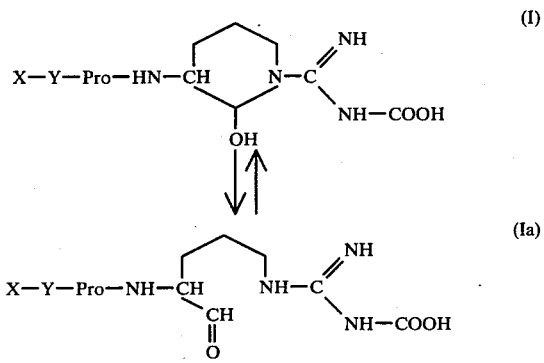

wherein

X is hydrogen, benzoyl or tert-butyloxycarbonyl, and

Y is D-phenylalanine, β-phenyl-D-lactic acid or D-allo-isoleucine residue or a pharmaceutically effective salt thereof.

2. The compound defined in claim 1, selected from the group consisting of
D-phenylalanyl-L-prolyl-N$^G$-carboxyl-L-arginine aldehyde, D-phenylalanyl-L-prolyl-N$^G$-carboxy-L-arginine aldehyde hemihydrochloride, tert-butyloxycarbonyl-D-phenylalanyl-L-prolyl-N$^G$-carboxyl-L-arginine aldehyde, benzoyl-D-allo-isoleucyl-L-prolyl-N$^G$-carboxy-L-arginine aldehyde, and β-phenyl-D-lactyl-L-prolyl-N$^G$-carboxy-L-arginine aldehyde.

3. A pharmaceutical composition for inhibiting the thrombin-fibrinogen reaction containing an effective amount of a compound as defined in claim 1 as the active agent in association with a pharmaceutically acceptable solid or liquid carrier.

4. A method of inhibiting the thrombin-fibrinogen reaction in a system susceptible thereto which comprises administering to the system an effective amount of a compound of the formula I or Ia

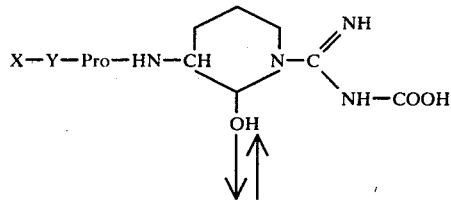

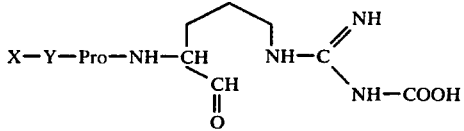

wherein
X is hydrogen, benzoyl or tert-butyloxycarbonyl, and
Y is a D-phenylalanine, β-phenyl-D-lactic acid or D-allo-isoleucine residue or a pharmaceutically effective salt thereof.

* * * * *